US012788838B2

(12) United States Patent
Brand et al.

(10) Patent No.: US 12,788,838 B2
(45) Date of Patent: Nov. 10, 2026

(54) VALIDATION OF MIXING PROCEDURES IN A DECONTAMINATION PROCESS

(71) Applicant: Tristel PLC, Snailwell (GB)

(72) Inventors: Thomas Brand, Snailwell (GB); Esther Jansen, Snailwell (GB); Paul Swinney, Snailwell (GB)

(73) Assignee: TRISTEL PLC, Newmarket (GB)

( * ) Notice: Subject to any disclaimer, the term of this patent is extended or adjusted under 35 U.S.C. 154(b) by 854 days.

(21) Appl. No.: 18/005,842

(22) PCT Filed: Jul. 19, 2021

(86) PCT No.: PCT/GB2021/051848
§ 371 (c)(1),
(2) Date: Jan. 17, 2023

(87) PCT Pub. No.: WO2022/018419
PCT Pub. Date: Jan. 27, 2022

(65) Prior Publication Data

US 2023/0338601 A1 Oct. 26, 2023

(30) Foreign Application Priority Data

Jul. 20, 2020 (GB) ...................................... 2011192

(51) Int. Cl.
*A61L 2/28* (2006.01)
*A61L 2/18* (2006.01)
*G06V 20/52* (2022.01)

(52) U.S. Cl.
CPC *A61L 2/28* (2013.01); *A61L 2/18* (2013.01); *G06V 20/52* (2022.01); *A61L 2202/14* (2013.01)

(58) Field of Classification Search
CPC ..... A61B 90/70; A61B 2090/702; A61L 2/28; A61L 2202/14; A61L 2/18; G06T 7/20;
(Continued)

(56) References Cited

U.S. PATENT DOCUMENTS 7,807,118 B2 * 10/2010 Green ........................ A61L 2/18
422/292
9,433,474 B2 9/2016 Swinney
(Continued)

FOREIGN PATENT DOCUMENTS

CN 1997406 A 7/2007
CN 108476202 A 8/2018
(Continued)

OTHER PUBLICATIONS

Coreys Corner Tips, “How to Scan / Read a QR 2019 2020 update No App Needed” https://www.youtube.com/watch v=DI1w_9c0q08 &feature=youtu.be (Uploaded Aug. 14, 2019). (Cited in copending U.S. Appl. No. 18/005,846).
(Continued)

*Primary Examiner* — Chineyere Wills-Burns
*Assistant Examiner* — Urooj Fatima
(74) *Attorney, Agent, or Firm* — Renner, Otto, Boisselle & Sklar, LLP

(57) ABSTRACT

Disclosed is a method for validating a mixing procedure in a process using a two-part disinfectant system. The disinfectant system comprises a first part comprising a first reagent in a carrier medium and a second part which is miscible with the first part and which comprises a second reagent in a carrier medium, and the first reagent and the second reagent will react when mixed to provide a disinfecting composition. The method comprises capturing a video stream of a work area in which the mixing procedure is carried out by a user, analysing the video stream to identify one or more mixing events in the video stream that correspond with the mixing procedure being correctly performed, determining, based on the or each identified mixing event, if the mixing procedure has been completed, and upon determining that the mixing procedure has been completed,
(Continued)

causing a corresponding indication to be provided to the user. The method may include alerting the user to potential errors and/or logging data to provide an audit trail.

17 Claims, 6 Drawing Sheets

(58) Field of Classification Search
CPC .......... G06T 2207/20084; G06V 20/44; G06V 40/28; G06V 20/52; G06V 20/40; G01C 11/00
See application file for complete search history.

(56) References Cited

U.S. PATENT DOCUMENTS

| | | | | |
|---|---|---|---|---|
| 12,249,144 | B2 | 3/2025 | Ferrante | |
| 2007/0094303 | A1* | 4/2007 | Zwingenberger | A61L 2/24 |
| 2012/0075464 | A1 | 3/2012 | Derenne et al. | |
| 2012/0212582 | A1 | 8/2012 | Deutsch | |
| 2015/0109442 | A1 | 4/2015 | Derenne et al. | |
| 2016/0175066 | A1* | 6/2016 | Swinney | G16H 40/20 700/242 |
| 2017/0344722 | A1 | 11/2017 | Ashoori | |
| 2019/0023476 | A1* | 1/2019 | Shabanova | B65D 81/3272 |
| 2019/0122047 | A1 | 4/2019 | Uemura | |
| 2019/0244340 | A1 | 8/2019 | Perron | |
| 2020/0043604 | A1* | 2/2020 | Singh | G06N 5/02 |
| 2022/0358761 | A1* | 11/2022 | Ferrante | G06V 10/764 |

FOREIGN PATENT DOCUMENTS

| | | | | |
|---|---|---|---|---|
| CN | 108734090 | A | 11/2018 | |
| CN | 109740488 | A | 5/2019 | |
| CN | 110263689 | A | 9/2019 | |
| CN | 111144262 | A | 5/2020 | |
| EP | 2404193 | A2 | 1/2012 | |
| GB | 2518239 | A | 3/2015 | |
| GB | 2546970 | A | 8/2017 | |
| JP | 2019500921 | A | 1/2019 | |
| JP | 2019079144 | A | 5/2019 | |
| JP | 2019084165 | A | 6/2019 | |
| JP | 2020064589 | A * | 4/2020 | |
| WO | 2005011756 | A1 | 2/2005 | |
| WO | 2005107823 | A1 | 11/2005 | |
| WO | WO-2006079822 | A1 * | 8/2006 | A61L 2/16 |
| WO | 2017/223159 | A1 | 12/2017 | |
| WO | 2020264367 | A1 | 12/2020 | |

OTHER PUBLICATIONS

GB Search Report under Section 17 issued for corresponding GB Application No. 2011192.8 dated Jan. 21, 2021.

GB Combined Search and Examination Report under Sections 17 and 18(3) issued for corresponding GB Application No. 2011193.6 dated Jan. 21, 2021.

GB Search Report under Section 17 issued for corresponding GB Application No. 2011194.4, dated Jan. 21, 2021.

International Search Report and Written Opinion of the International Searching Authority (ISA) issued for corresponding International Patent Application PCT/GB2021/051848, dated Oct. 22, 2021.

SureWash Technology: Interactive Hand Hygiene Training, <https://surewash.com/news/surewash-technology-interactive-hand-hygiene-training/>, accessed on the internet on Jan. 13, 2026.

* cited by examiner

Fig. 7
Fig. 8
Fig. 9
foam
folding
scrunching

VALIDATION OF MIXING PROCEDURES IN A DECONTAMINATION PROCESS

This application is a National Phase of International Application No. PCT/GB2021/051848, filed Jul. 19, 2021, which claims priority to United Kingdom Application No. 2011192.8, filed Jul. 20, 2020, each of which is hereby incorporated herein by reference in its entirety.

BACKGROUND a. Field of the Invention

The present invention relates to methods and apparatus for validating procedural steps during use of a decontamination system. The invention is particularly for use in validating processes for disinfecting medical devices and surfaces in clinical environments.

b. Related Art

Effective decontamination of medical devices, surfaces and other objects in clinical environments is essential to ensure patient safety. Several highly-effective disinfectant systems have been developed to address this need.

For example, WO 2005/011756 discloses a two-part disinfectant system. The disinfectant system comprises a first part having a first reagent in a carrier medium and a second part which is miscible with the first part and which comprises a second reagent in a carrier medium. The first reagent and the second reagent react when mixed to provide a disinfecting composition. In a preferred implementation, one of the parts is an acidic solution and the other of the parts is a solution containing sodium chlorite or sodium chlorate, and a disinfecting composition comprising chlorine dioxide is produced when the two parts are mixed. The first part, known as an activator, is contained in a pump dispenser whereby it may be dispensed as a fluid, preferably as a foam, and the second part is absorbed or impregnated in at least one fabric member in a sealed container. To prepare a disinfecting wipe, a user removes an impregnated wipe from the container, and applies a portion of foam from the dispenser to the wipe. To facilitate mixing of the reagents in the foam and the wipe, the user may fold the wipe to surround the foam and crush or rub the folded wipe by scrunching before opening it out.

WO 2005/107823 describes a decontamination system (shown in FIG. 1) suitable for the reprocessing of non-lumened medical devices using a manual three-wipe disinfection process. An example system includes a box 10 containing sachets 11 of pre-clean wipes, a disinfecting system 12 including a dispenser 14 and sachets 16 of disinfecting wipes as discussed above, and a box 18 containing sachets 20 of sterile rinse wipes. The pre clean wipe is used to wipe an item such as an endoscope which is to be decontaminated. The two-part disinfecting system 12 (combination of a wipe and activator foam) is used for sterilising or disinfecting the item and the sterile rinse wipe is used to remove any chemical residue. All disinfection details can be recorded in an accompanying audit trail book to allow full procedural traceability.

To ensure that a decontamination system of this type is fully effective, it is necessary for the user to follow correctly a specific sequence of steps. An example of such a sequence is shown in FIG. 2.

In step 101, a pre-clean wipe is removed from its sachet 11. In step 102, the device is wiped with the pre-clean wipe, starting at the cleanest part of the device (such as a handle) and wiping towards the dirtiest or most contaminated part (such as an invasive distal part).

In step 103, a disinfectant wipe is removed from its sachet 16 and opened out; then in step 104 the correct quantity of activator foam is dispensed onto the wipe (typically measured by operating the dispenser 14 a predefined number of times). In step 105, the wipe is folded to enclose the foam and then scrunched for a predefined period of time to thoroughly mix the two parts of the disinfectant system. In step 106, the device is wiped with the activated disinfectant wipe, again starting at the cleanest part and moving towards the dirtiest part.

In step 107, a rinse wipe is removed from the sachet 20, and in step 108 the device is wiped with the rinse wipe, again in the clean-to-dirty direction.

In step 109, the decontaminated device is placed into a designated clean area, to avoid re-contamination of the device that might otherwise occur.

Any errors made by the user can compromise the decontamination process. Examples of such errors include selection of the wrong sachet 11, 16, 20 in any of steps 101, 103 or 107, wiping in the wrong direction or too quickly in any of steps 102, 106 or 108, dispensing an insufficient amount of activator in step 104, and scrunching the wipe for too short a time in step 105.

The use of an audit trail book or audit trail software can be helpful in avoiding such errors. However, such measures are typically reliant on user input, and are not readily able to verify directly that some of the steps have been correctly performed.

Against that background, it would be desirable to provide solutions for validation of procedures during decontamination processes that are less reliant on user input and that are able directly to validate more of the steps in a decontamination process.

SUMMARY OF THE INVENTION

From a first aspect, the present invention resides in a method for validating a mixing procedure in a process using a two-part disinfectant system. The disinfectant system comprises a first part comprising a first reagent in a carrier medium and a second part which is miscible with the first part and which comprises a second reagent in a carrier medium, and the first reagent and the second reagent will react when mixed to provide a disinfecting composition. The method comprises capturing a video stream of a work area in which the mixing procedure is carried out by a user, analysing the video stream to identify one or more mixing events in the video stream that correspond with the mixing procedure being correctly performed, determining, based on the or each identified mixing event, if the mixing procedure has been completed, and upon determining that the mixing procedure has been completed, causing a corresponding indication to be provided to the user.

With this method, validation of the mixing procedure for a two-part disinfectant system can be based on the automated assessment of a user's actions through analysis of the video stream, which is of substantial benefit in ensuring that the user completes the mixing procedure correctly. The method provides the user with a positive indication that the mixing procedure has been successfully completed, thereby ensuring that the disinfecting composition is optimally effective and improving user confidence.

Analysing the video stream preferably comprises using a trained neural network to identify the mixing event or at least one of the mixing events. With suitable training, the neural network is able to reliably and rapidly identify the mixing events as they are performed by the user.

The first part and/or the second part of the disinfectant system may comprise an indicator component that undergoes a colour change upon mixing of the first part and the second part. In this case, the mixing event or one of the mixing events to be identified in the image analysis step may comprise the colour change. It is therefore possible through image analysis to identify that the colour change has occurred fully and uniformly, indicating that the mixing procedure has been successful.

The mixing event or one of the mixing events identified in the image analysis step may comprise the application of a predetermined quantity of the first part of the disinfectant system to a predetermined quantity of the second part of the disinfectant system.

The first part of the disinfectant system may be contained in a dispenser whereby it may be dispensed as a fluid, and in this case the mixing event or one of the mixing events may comprise dispensing of the fluid from the dispenser. The second part of the disinfectant system may be absorbed or impregnated in a wipe, and in this case the mixing event or one of the mixing events may comprise folding or scrunching of the wipe after application of the first part to the wipe. In this way, the method can verify that the user has mechanically manipulated the wipe in the correct way to ensure complete distribution and mixing of the first part throughout the wipe.

In another example, the first and second parts of the disinfectant system may be both be dispensed as foams, either separately or in a pre-mixed state, and the mixing event or one of the mixing events may comprise mixing of the foams (for example by stirring, or by dispensing the foams onto a wipe and folding or scrunching of the wipe) and/or allowing the mixed foams to dwell.

Determining if the mixing procedure has been completed may comprise determining a cumulative time for which the mixing event or at least one of the mixing events has been performed, and comparing the cumulative time to a predetermined minimum mixing time. For example, when the first part of the disinfectant system is contained in a dispenser and the second part is a wipe, determining if the mixing procedure has been completed preferably comprises determining, based on at least two identified mixing events, if (a) the predetermined quantity of the first part of the disinfectant system has been applied to the wipe and (b) the wipe has subsequently been folded or scrunched for at least the predetermined minimum mixing time. The method may comprise determining the minimum mixing time required, for example by retrieving a predetermined mixing time from a memory. Optionally, determining the minimum mixing time required may comprise selecting or computing the minimum mixing time based on a determined environmental temperature or other environmental or system parameters.

Alternatively, or in addition, determining if the mixing procedure has been completed may comprise determining whether a plurality of different mixing events have been performed in a predetermined sequence. This sequence of different mixing events could include, for example, first dispensing a quantity of a foam-based first part onto a wipe of the second part, then folding the wipe over the foam, then scrunching the wipe for a predetermined time. To verify that the correct products are being used in the mixing procedure, the mixing event or at least one of the mixing events may comprise the presentation of a container containing the first part and/or the presentation of a container containing the second part.

In addition to providing a positive indication that the mixing procedure has been correctly completed, it is also possible for the method to provide an indication that a possible error has occurred, allowing the user to take corrective action or, if the error is sufficiently severe, to abandon and re-start the procedure if necessary. To that end, the method may further comprise, when analysing the video stream, identifying one or more alert events in the video stream that correspond with potential errors being made during performance of the mixing procedure, and upon identification of an alert event, causing a corresponding alert to be provided to the user.

For example, the alert event or one of the alert events may comprise shaking a container containing the first part or shaking a container containing the second part. In particular, when the first part and/or the second part is dispensed as a foam, shaking the dispenser before dispensing the foam can adversely affect the volume of product delivered with each activation of the dispenser. In this case, the alert provided to the user may prompt the user to stop shaking the container. The alert event or one of the alert events may comprise selecting the wrong product for the step that is about to be performed. In this case, the alert provided to the user may instruct the user to select the correct product.

In another example, the alert event or one of the alert events comprises non-visibility in the work area of the user's hands, the first part of the disinfectant system and/or the second part of the disinfectant system. In this way, an alert can be provided to instruct the user to ensure that the actions relating to the mixing procedure are performed within the field of view of the video stream.

The method may also provide a means for electronically logging information concerning the mixing procedure. In particular, the method may comprise electronically logging that the mixing procedure has been completed. When the method includes identifying alert events, the method may comprise electronically logging that an alert event has been identified. The method may include electronically logging information concerning the first part of the system and/or the second part of the system, in which case analysing the video stream may comprise identifying, in the video stream, said information concerning the first part of the system and/or the second part of the system, for example by reading a machine-readable code or looking up the information after identifying the product being used. The information concerning the first part of the system and/or the second part of the system may comprise at least one of: a type of the first part or the second part; a lot or batch number; a date of manufacture; a use-by or expiry date.

The invention also extends, in a second aspect, to an apparatus for validating a mixing procedure in a process using a two-part disinfectant system, comprising a camera system for capturing a video stream of a work area in which the mixing procedure is carried out by a user, an output device for providing audio, textual and/or visual indications to the user, an image analysis module configured to receive the video stream and to identify one or more mixing events in the video stream that correspond with the mixing procedure being correctly performed, and a validator module configured to determine, based on the or each identified mixing event, if the mixing procedure has been completed, and to cause the output device to provide a corresponding indication to the user upon determining that the mixing procedure has been completed. Preferably, the image analysis module comprises a neural network-based classifier trained to recognise the one or more mixing events in the video stream. The apparatus may further comprise a logging module configured to electronically log that the mixing procedure has been completed. Conveniently, the apparatus may comprise a smartphone or tablet computer device.

In a further aspect, the invention resides in the use of an apparatus according to the second aspect to validate a mixing procedure in a process using a two-part disinfectant system in accordance with the method of the first aspect.

The invention also resides in a decontamination system comprising a disinfectant system including a first part comprising a first reagent in a carrier medium and a second part which is miscible with the first part and which comprises a second reagent in a carrier medium, in which the first reagent and the second reagent will react when mixed to provide a disinfecting composition, and an apparatus according to the second aspect of the invention for validating a mixing procedure in use of the disinfectant system.

The present invention can be used to validate a mixing procedure in substantially any decontamination process in which the mixing procedure is required to produce an active disinfecting or cleaning composition. The decontamination process may also include other steps or procedures, such as use of a pre-clean stage and/or a rinsing stage, and embodiments of the present invention may be extended to validate one or more of the associated procedures in addition to the mixing procedure. The decontamination process may be used to decontaminate a medical instrument or device, in which case embodiments of the invention may validate the correct cleaning procedure for the device in addition to the mixing procedure.

Preferred and/or optional features of each aspect of the invention may also be used, alone or in appropriate combination, in the other aspects also.

In the context of this specification, the term "validating a procedure" is used to refer to confirming by suitable means that one or more particular steps have been taken or avoided, and/or that one or more specific products have been used, when carrying out the procedure in question. The procedure that is validated need not encompass an entire process for decontaminating a device, object or surface, but may instead be only a part of a longer decontamination process.

The term "decontamination process" is used to refer to a sequence of steps by which an object or surface is cleaned, prepared for cleaning, disinfected, sterilised, rinsed and so on, including steps for the preparation of materials and products for use in such activities. The term "decontamination procedure" is used to refer to a single such step within a decontamination process, a combination of such steps as a sub-set of a longer decontamination process, or all of the steps of a decontamination process, as the context demands.

BRIEF DESCRIPTION OF THE DRAWINGS

Embodiments of the present invention will now be described, by way of example only, with reference to the accompanying drawings, in which like reference numerals are used for like features, and in which.

DESCRIPTION OF THE PREFERRED EMBODIMENTS

Embodiments of the present invention provide methods and apparatus for automatically or semi-automatically validating various procedures or steps that a user must undertake when performing a decontamination process. The following examples refer to the decontamination system and corresponding decontamination process described above with reference to FIGS. 1 and 2, but embodiments of the invention are equally applicable to other decontamination systems and processes.

Figure 3:
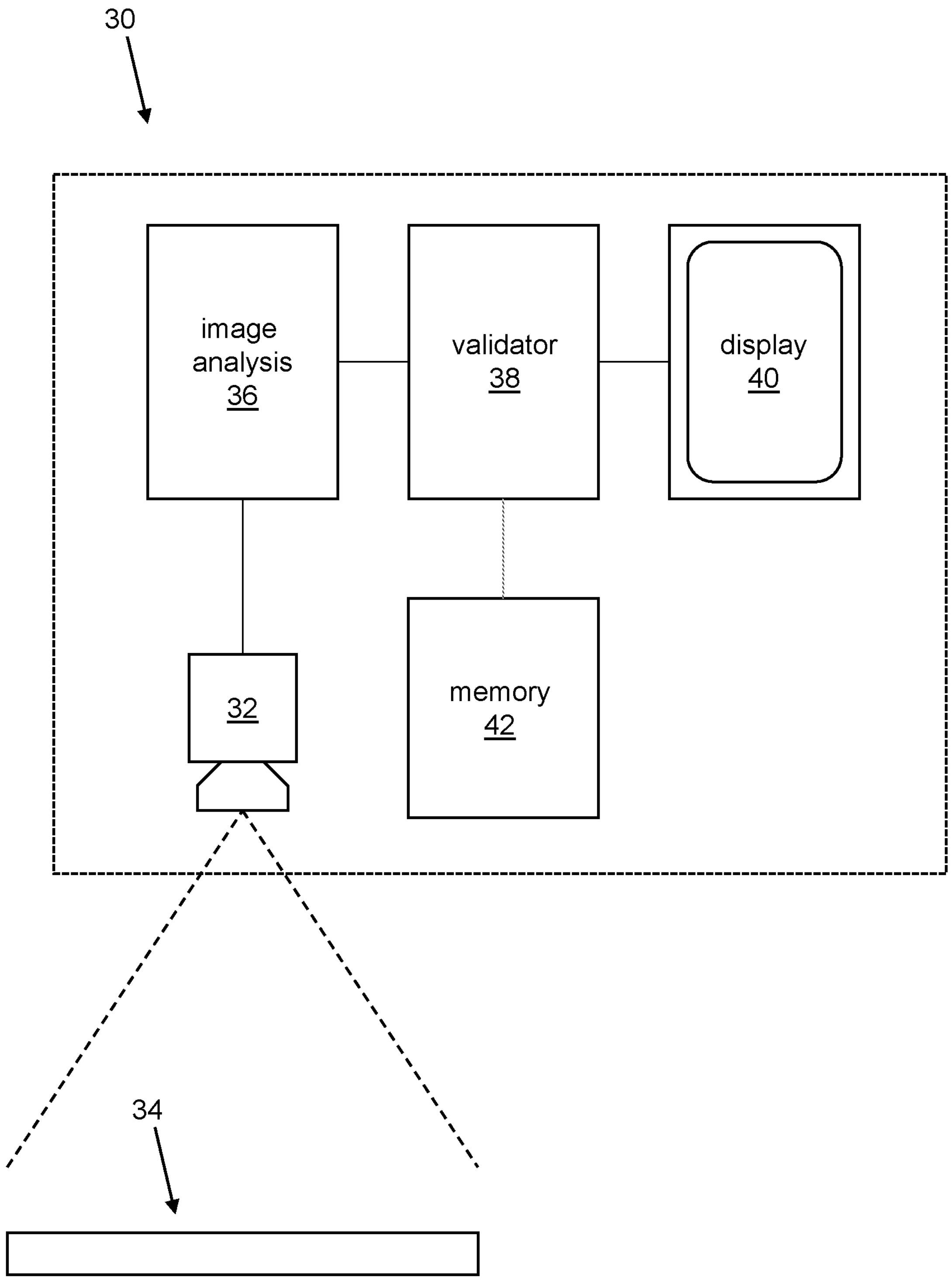
FIG. 3 shows an apparatus for validating a decontamination procedure.

FIG. 3 is a schematic illustration of an apparatus for validating a procedure. In this example, the apparatus comprises a portable device 30 having a camera system 32 for capturing a video stream of a work area 34.

The camera system 32 outputs the video stream to an image analysis module 36. As will be explained in more detail below, the image analysis module 36 analyses the video stream to identify when certain pre-defined events or actions are being performed in the work area. The image analysis module 36 outputs corresponding event data to a validator module 38.

The validator module 38 analyses the received event data to determine whether a predefined procedure has been correctly completed, or if any potential errors are being made. After making such a determination, the validator module 38 causes a display 40 to provide a corresponding indication to the user. The validator module 38 may also cause an indication to be provided via an audio output (not shown), such as a loudspeaker or headphone output.

The validator module 38 is also configured to log data in a memory 42. In this way, the validator module 38 can record, in the memory 42, that one or more predefined procedures have been correctly completed and/or that one or more potential errors have been observed in the video stream.

This logged event information may be correlated with additional information, such as a user name and other user details, patient details, a location in which the procedure is being carried out, the type of device, surface or other item being decontaminated, the serial number of a device, details of the decontamination system and its constituent parts, such as serial, batch or lot numbers, dates of manufacture, expiry dates and so on. Such additional information may be input by a user through a suitable interface (not shown), typically a touch-screen, may be captured by reading a barcode or matrix code presented to the camera, or may be determined by analysis of the video stream. In the latter case, the image analysis module 38 may for example be configured to recognise the containers (i.e. the sachets 11, 16, 20 and dispenser 14) that contain the various products used in the decontamination system, and the validator module 38 may be configured to retrieve stored product type information corresponding to each identified container and to record that information along with the logged event information.

In these ways, the memory 42 stores a partial or full audit trail of the decontamination process that can be stored in the memory 42 for subsequent retrieval, and/or transmitted to a server or another device using a suitable communication protocol or network for record-keeping purposes.

The apparatus may be provided as a self-contained, portable device 30, such as a smartphone or tablet computer.

Conveniently, conventional smartphones, tablet computers and similar devices already include a camera system, data storage, a display, an audio output and communication devices for network connectivity, along with a processor that can be configured to execute suitable instructions to cause the methods described herein to be performed. The image analysis module 36 and validator module 38 are therefore preferably realised in software for execution by the processor. The software may be embodied as an installable application that runs within a device operating system environment. The image analysis module 36 and/or the validator module 38 may also be provided, in whole or in part, by cloud-based services with which the device 30 is configured to communicate.

The camera system may comprise a single camera or multiple cameras, and it is conceivable that non-visible light cameras (such as thermal or depth cameras) could be provided to feed additional data to the image analysis module 36.

The device 30 is preferably mounted on a suitable stand, with the camera apparatus 32 directed towards the work area 34, to free both of the user's hands for performing the decontamination process. However, in some cases it may also be possible for the user to hand-hold the device 30 for some or all of the process.

The image analysis module 36 can use any suitable method to analyse the video stream, but preferably a machine learning approach is used. For example, the image analysis module 36 may employ a trained artificial neural network (such as a convolutional neural network and/or a recurrent neural network) to identify, classify or characterise objects and actions that appear or occur in the work area 34 on a frame-by-frame basis or across multiple frames. Supervised learning can be readily employed by training the network using video footage and/or images of multiple versions of the events to be identified. Semi-supervised learning, active learning and user feedback input can also be used, to achieve ongoing improvements in accuracy. In embodiments, these approaches can be used to refine the neural network for increased accuracy with a particular user and/or a particular environment or work area.

Various suitable neural network models will be familiar to those skilled in the art of machine learning-based video analysis and will not be discussed in detail here. One suitable neural network architecture is based on MobileNet, which provides a convolutional neural network for extracting framewise features from the video stream. This is combined with an LTSM (long short-term memory) recurrent neural network to aggregate temporal information (i.e. movement between frames). Other possibilities include two-stream convolutional neural networks.

It is to be noted that, in each implementation of the invention, the image analysis module 36 need only be able to identify a relatively small number of different events to allow the validator module 38 to determine accurately whether the procedure in question has been correctly performed or whether potential errors have occurred.

Some of the events identified by the image analysis module 36 may correspond to a step in the decontamination procedure being correctly performed. Examples of such "decontamination events" include picking up the correct product, correctly combining and mixing the two parts of the disinfectant system, applying a decontaminating composition to a device in the correct way, and so on. Others of the events may correspond to potential errors being made by the user. Examples of such "alert events" include selecting the wrong product for a particular stage in the procedure, cleaning a device too quickly or in the wrong direction, applying the wrong quantity of one of the parts of the two-part disinfectant system to the other part, mixing the two parts incorrectly or for an insufficient time, shaking the dispenser before use, placing the device in a designated clean region of the work area before decontamination or in a designated dirty region of the work area after decontamination, failure to wear gloves and/or other protective equipment, and so on.

The neural network is trained for all of the events or tasks to be identified in a multi-task learning environment. For the characterisation of each event or task, a hierarchical representation of the outcome may be used. For example, the task of detecting the type of product contained within a sachet is conditional on observing the sachet. In this way, the outcomes are forced to be consistent.

A training dataset covering all of the events to be identified can be produced from multiple demonstration videos in which events are labelled, including multiple examples showing the same event with suitable variations to reflect the main sources of variability expected in use. Such variations may include variations in cameras, portrait or landscape orientation, camera tilt, distance between the camera and the work area, background colour and material, lighting colour, source, intensity and direction, glove colour, user's skin colour, gender, handedness and proficiency in the usage of the products, and so on. Further variability can be synthetically added by data augmentation, for example to introduce variability in brightness, different light conditions, horizontal and vertical flips to simulate camera orientation, shearing and rotation to simulate camera tilting. For subsequent testing, a testing dataset may be used in which different demonstration videos, for example with a different user and/or different settings of the above variables, are provided compared with those in the training dataset.

To facilitate learning of procedures without labels, a self-supervised learning approach can added. For example, the frame ordering in videos showing the correct procedure can be shuffled and the network can then be trained to recognise the original frame order. Other examples of self-supervised learning include image inpainting (removing a part of an image and training the network to reconstruct it, to learn the structure of the objects/medical device), and image recolouring (to make the model learn a colour transition upon mixing and/or an expected colour of a sachet or other container).

The image analysis module 36 outputs the identified decontamination events and the identified alert events to the validator module 38. The validator module 38 may determine that each step in a procedure has been correctly performed when the output of the image analysis module 36 indicates that the required procedure-specific decontamination event or events have occurred. To that end, the validator module 38 may employ a finite state machine or a hidden Markov model to convert the framewise prediction of events output from the image analysis model 36 to a global assessment of the sequence of steps performed in the procedure. When more than one decontamination event is required for the correct performance of a procedure, the validator module 38 may check that all of the required events have occurred, and that they have occurred in the correct order. The validator module 38 may also check that no alert events have occurred, or that the error corresponding to an identified alert event has been subsequently corrected (for example through the observation of a corresponding decontamination event immediately afterwards). Some alert events may correspond to immediately-correctable errors, such as picking up an incorrect product, or having the user's hand or parts of the decontamination system obscured or positioned outside the field of view, while others, such as applying the incorrect product to a device, may require the decontamination process to be re-started.

In addition to the ability to log these outcomes in the memory 42 as part of an audit trail, the device 30 advantageously can also provide immediate feedback to the user, by the display of graphical and/or textual indications on the display 40 and/or by the playing of sounds and/or speech through the audio output of the device. In this way, when each step of a specific procedure is correctly performed, an indication can be provided to the user to confirm both that the step has been completed, and that the device 30 has recorded that fact. Similarly, if a potential error is identified, giving rise to an alert event, the user can be prompted by a suitable indication to take suitable corrective action.

The device 30 can also be used to guide a user through the procedure, by providing prompts or instructions relating to the next steps to be performed using the display and/or the audio output. For example, the validator module 38 may cause an instruction relating to the next step of the procedure to be displayed after a particular decontamination event has been identified. In another example, where a particular action must be performed for a specific time, the validator module 38 may cause a timer to be displayed as a guide for the user when an event indicating the start of that action is identified.

To enable the validator module 38 to operate in these ways, suitable procedure data relating to each specific procedure can be stored in the memory 42. The procedure data may include, for example, a list of required events and the order in which they must be undertaken, predefined times or other parameters for individual steps, and a list of possible alert events that correspond to potential errors. The validator module 38 can compare the identified decontamination and alert events to the stored procedure data to determine if each step in the procedure has been performed correctly or if errors have occurred, and can retrieve information about the expected next step to trigger the display of instructions or other actions such as the start of countdown timer. The memory 42 may store procedure datasets for a plurality of possible procedures, so that the validator module 38 can select whichever procedure dataset is appropriate for the procedure being performed. The procedure data may include corrections to allow for adjustment of parameters to compensate for environmental factors, such as temperature and humidity, which may be determined by the device 30 using suitable sensors and/or input by the user.

Example 1

Figure 1:
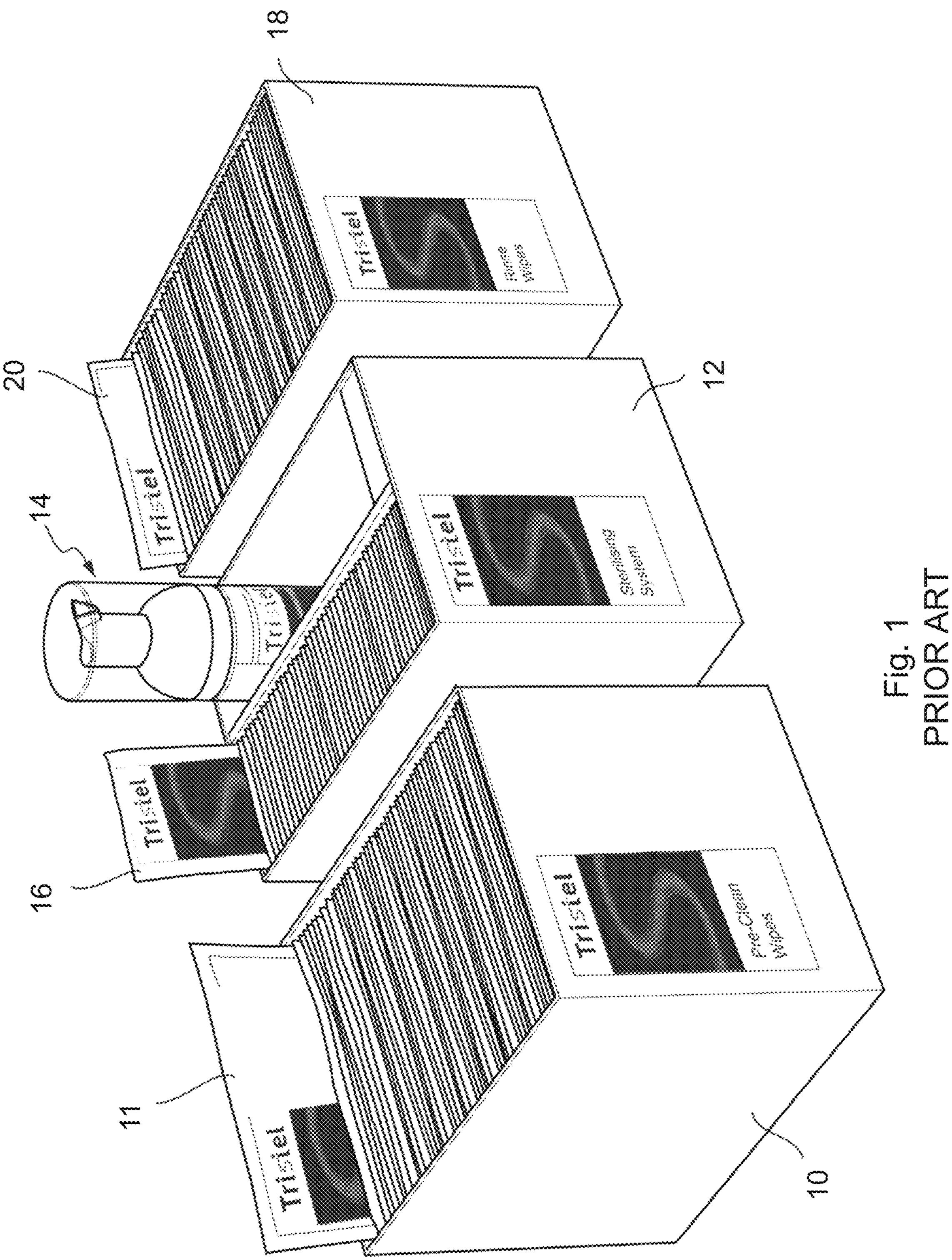
Fig. 1 PRIOR ART
FIG. 1 shows a known decontamination system to which embodiments of the invention can be applied.
Figure 2:
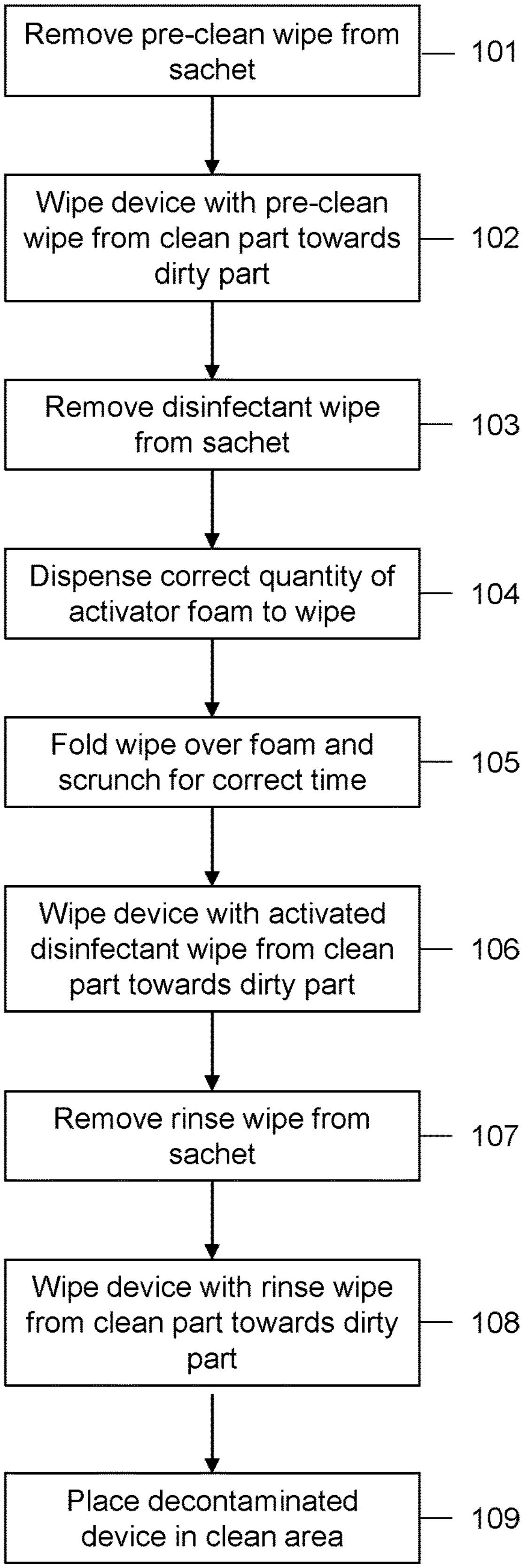
Fig. 2 (PRIOR ART)
FIG. 2 shows a sequence of steps in a decontamination process using the system of FIG. 1.

The following example describes the use of the device 30 to validate a decontamination process for a medical device in which a decontamination system of the type shown in FIG. 1 is used. The medical device may for example be an endoscope, nasendoscope, transvaginal probe or similar device, with a proximal handle part and a distal invasive end part. FIGS. 4 to 12 show example frames captured by the camera system 32, which in this case is positioned above the work area. As an aid to understanding, the output provided by the image analysis module 36 is indicated in the top left corner of each image.

Step 1. First, the type of medical device to be decontaminated is identified and logged. This may be done automatically by image analysis of the video stream when the device is placed in the work area, in which case the user is subsequently prompted to confirm that the medical device type has been correctly identified. Alternatively, the medical device type may be entered by the user, for example by selection from a list of predefined options.

Step 2. The unique serial number of the device is captured and logged. Again, this may be done by image analysis, for example by capturing a barcode or matrix (QR) code or by reading text directly; alternatively, the serial number may be entered by the user. Once captured, the serial number is checked to ensure that it is possible for that type of device.

Step 3. The device 30 displays a prompt to the user to prepare a pre-cleaning wipe.

Step 4. The device 30 identifies and acknowledges that an appropriate pre-cleaning product is to be used. The image analysis module 36 identifies, as a decontamination event, the presence in the work area of an approved pre-clean wipe sachet as it is presented to the camera by the user. The pre-clean wipe sachets are differentiated from the sachets used later in the process by differently-coloured indicia, so that the image analysis module 36 can distinguish between the various sachets. If a sachet is presented that does not correspond to the expected pre-clean wipe sachet, an alert event is identified and the device 30 indicates that the wrong sachet has been selected. The identified sachet type may also be checked against a stored stock list of suitable pre-cleaning products or user-inputted systems. The presence of the pre-cleaning product, optionally along with the type of the product and further information such as a batch number or expiry date, is logged.

Step 5. Image analysis is used to identify the proximal handle part of the device and the distal invasive end part of the device.

Step 6. The device 30 displays a prompt to the user to commence pre-cleaning of the device, and then monitors the video stream for possible alert events. For example, if pre-cleaning starts from the dirtier invasive end part instead of the cleaner proximal handle part, or if the wipe is moved in the wrong direction, an error will be indicated. Similarly, if the pre-cleaning action performed by the user is too fast or conflicts with pre-determined product-specific instructions for use data, an error will be indicated.

Step 7. When the image analysis module 36 identifies that the device has been pre-cleaned from the clean part to the dirty part in accordance with product specific user instructions without alert events being identified, the device 30 provides an acknowledgement to the user.

Step 8. The device 30 prompts the user to prepare a disinfectant wipe.

Figure 4:
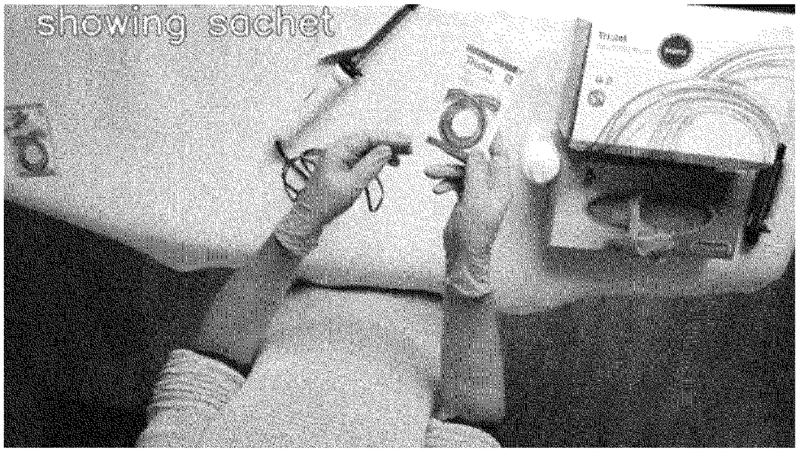
FIGS. 4 to 12 are images captured from a video stream showing events taking place during a decontamination process for a medical device.

Step 9. The device 30 identifies and acknowledges that an appropriate disinfectant product is to be used. As in step 4 above, the image analysis module 36 identifies, as a decontamination event, the presence in the work area of an approved disinfectant wipe sachet as it is presented to the camera by the user. This is shown in FIG. 4. If a sachet is presented that does not correspond to the expected disinfectant wipe sachet, an alert event is identified and the device 30 indicates that the wrong sachet has been selected. The identified sachet type may also be checked against a stored stock list of suitable disinfectant products or user-inputted systems. An additional verification check cross-references the disinfectant product against the previously used pre-clean product to ensure they are approved for use together. The presence of the disinfectant wipe, optionally along with the type of the product and further information such as a batch number or expiry date, is logged.

Step 9A. The device 30 identifies and acknowledges that an appropriate disinfectant activator product is to be used.

Here, the image analysis module 36 identifies, as a decontamination event, the presence in the work area of an approved dispenser of the activator foam as it is presented to the camera by the user. The same checks may be applied for the activator product in this step as in step 9 above.

Figure 5:

Step 9B. The device 30 prompts the user to apply the activator foam to the wipe, and then monitors the video stream for the following events:

(a) A disinfectant wipe has been removed from the sachet and is visible in the work area (see FIG. 5).

Figure 6:
Figure 7:
Figure 8:
Figure 9:

(b) Two aliquots of foam have been added to the wipe (two aliquots corresponding to the correct quantity to be added to a single wipe, in this example). FIG. 6 shows the identification of the step of dispensing foam onto the wipe from the dispenser, and FIG. 7 shows the aliquots of foam on the wipe.

(c) The wipe has been folded (FIG. 8) and scrunched (FIG. 9) to distribute the foam throughout the wipe for at least a minimum period of time to ensure full activation of the disinfecting composition.

Figure 10:

(d) The wipe has been unfolded, has a uniform appearance, and is ready for use (FIG. 10).

After each event has been identified, the device 30 logs the event, displays an acknowledgement that the corresponding step has been correctly performed, and prompts the user to perform the next step. If any errors are made, such as fewer or more aliquots of foam being dispensed than are required, an alert is displayed to the user. Optionally, the size of each aliquot is checked to ensure that the pump has been correctly operated each time.

Step 10. Image analysis is again used to identify the proximal handle part of the device and the distal invasive end part of the device.

Figure 11:

Step 11. The device 30 displays a prompt to the user to commence disinfection of the device, and then monitors the video stream for possible alert events. FIG. 11 shows identification of the disinfecting wipe being applied to the device. If disinfection starts from the invasive end part instead of the cleaner proximal handle part, or if the wipe is moved in the wrong direction, an error will be indicated.

Similarly, if the disinfection action performed by the user is too fast or conflicts with pre-determined product specific instructions for use data will signal, an error will be indicated.

Step 12. The image analysis module 36 identifies when the disinfecting wipe has been wiped over all of the medical device. The device 30 then displays a countdown timer and starts a countdown for the contact time of the disinfection process. If, during the wiping process, wiping is stopped or interrupted or otherwise not conducted at a uniform speed along the length of the device, or if the wipe is removed from the device, an error will be indicated. Similarly, if the user touches the device or another item (such as a wipe) contacts the device during the countdown, an error will be indicated.

Step 13. When the image analysis module 36 identifies that the device has been disinfected from the clean part to the dirty part in accordance with product specific user instructions, and that the required contact time has been observed, without alert events being identified, the device 30 provides an acknowledgement to the user.

Step 14. If the products used in the precleaning and disinfection stage do not require final rinsing the device 30 will indicate that the decontamination process is complete. If the predefined parameters indicate that the product set used requires rinsing the device 30 will prompt to proceed to step 15.

Step 15. If rinsing is required, the device 30 will prompt the user to prepare a rinse wipe.

Step 16. The device 30 identifies and acknowledges that an appropriate rinse wipe product is to be used. The image analysis module 36 identifies, as a decontamination event, the presence in the work area of an approved rinse wipe sachet as it is presented to the camera by the user. If a sachet is presented that does not correspond to the expected rinse wipe sachet, an alert event is identified and the device 30 indicates that the wrong sachet has been selected. The identified sachet type may also be checked against a stored stock list of suitable rinse products or user-inputted systems, and may be checked for compatibility with the pre-clean and disinfectant wipes used in the previous steps. The presence of the rinse product, optionally along with the type of the product and further information such as a batch number or expiry date, is logged.

Step 17. Once again, image analysis is used to identify the proximal handle part of the device and the distal invasive end part of the device.

Step 18. The device 30 displays a prompt to the user to commence rinsing of the device, and then monitors the video stream for possible alert events. For example, if rinsing starts from the invasive end part instead of the cleaner proximal handle part, or if the wipe is moved in the wrong direction, an error will be indicated.

Step 19. When the image analysis module 36 identifies that the device has been rinsed from the clean part to the dirty part in accordance with product specific user instructions without alert events being identified, the device 30 provides an acknowledgement to the user.

Step 20. At the end of the process, the device 30 provides a successful process validation code (if required by the user) and logs the details of the process in the memory 42. It is also possible for the device 30 to log the recommended storage time before re-disinfection is required.

Figure 12:
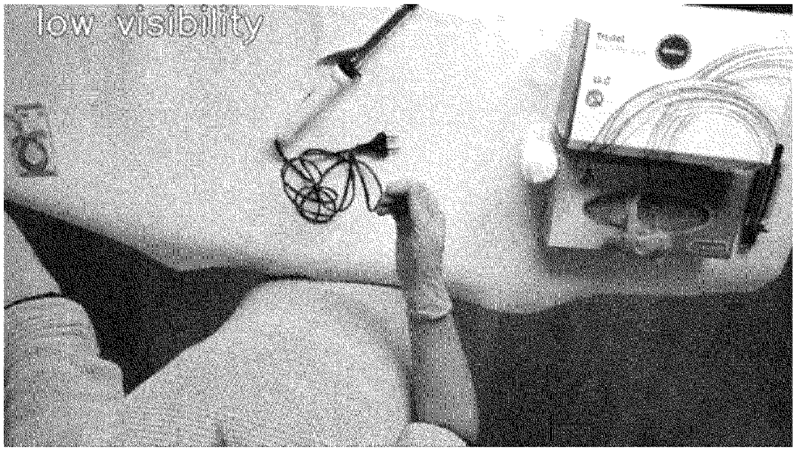

The image analysis operations in the above steps rely upon the procedures being carried out within the field of view of the camera system. Accordingly, throughout all of the steps, the device 30 will provide an error indication to the user if the user's hands are not visible in the video stream because they are obscured or outside the visible area, as shown in FIG. 12.

In the above steps, an "approved" product means that that the product is intended for use for the intended application, approved by the user's establishment for the intended application and/or approved by the medical device manufacturer.

Example 2

In this example, the two-part disinfectant system 12 includes, in one or both of the parts, a component that exhibits a colour change when the two parts are mixed. In this case, the colour change can be identified in the video stream to verify the complete mixing of the two parts of the disinfectant system 12, in addition to the verification of the physical mixing process described in step 9B of Example 1.

Accordingly, the verification steps associated with the correct preparation of an activated disinfecting wipe in this example are as follows:

Step 1. Identifying a disinfecting wipe sachet, checking compatibility, and acknowledging to the user.

Step 2. Identifying an activator foam dispenser, checking compatibility, and acknowledging to the user.

Step 3. Identifying a non-activated wipe when removed from the sachet. At this stage, an error is indicated if the wipe is not of the correct starting colour.

Step 4. Identifying the dispensing of the foam to the wipe and, optionally, the correct number of aliquots of foam.

Step 5. Identifying the folding and scrunching of the wipe for the appropriate time.

Step 6. Identifying that, after scrunching, the disinfecting wipe is of the correct post-change colour, and that the colour is uniform across the wipe.

It is also possible that the colour change alone could be used to verify complete mixing of the two parts of the disinfectant system, in which case steps 4 and 5 could be omitted.

It will be understood that not all of the steps set out in the examples above need to be identified as events by the image analysis module 36 and taken into account by the validation module 38 in order for the device 30 to reliably validate the respective processes. In embodiments of the invention, recognition of some of the steps can be omitted. Similarly, additional steps not discussed in these examples may be recognised and used in the validation method.

The above examples are merely illustrative of decontamination processes that can be validated by the present invention. Many variations are possible.

For example, WO 2006/079822 A1 describes a disinfecting system in which the first and second reagents are each carried in aqueous media to which foam promoters are added, so that both the first and second parts of the system are dispensed as first and second foams respectively. The first and second foams are mixed to generate the disinfecting composition, which may then be applied to an item or surface to be disinfected directly or with a wipe. The first and second foams may be dispensed separately and manually mixed together, or may be dispensed simultaneously from a dispenser that pre-mixes the foams during dispensing. In such a system, the verification process could include identifying the or each foam dispenser, identifying the dispensing of suitable quantities of each foam (or, when applicable, the pre-mixed foam), identifying that a manual mixing process has been performed (such as stirring the foams for a predefined period, or scrunching them together on a wipe), identifying that the mixed foams have been allowed to dwell for a predefined period before use, and/or applying the foams separately or in a mixed form to a wipe or other substrate. As in Example 2 above, one or both of the parts may include a component that exhibits a colour change when the two parts are mixed, in which case the verification process may comprise identifying that, after mixing, the mixed foam is of the correct post-change colour, and that the colour is uniform within the foam.

As already indicated, the process of Example 1 may omit the rinse stage if it is not necessary in a particular application. In this case, only the pre-clean and disinfection stages would be used. It is also conceivable that only the disinfection stage and the rinse stage could be used, with the omission of the pre-clean stage. When at least two stages are used, using two different products, the validation process preferably includes the steps of identifying each product being used and verifying that they are being used in the correct order.

It is also possible for a single-stage disinfection or decontamination process to be validated using the approach described above. For example, in some applications, the use only of a cleaning or disinfecting wipe may be necessary to provide the required degree of decontamination. In such a case, the validation process may focus primarily on determining that the wipe has been correctly applied to a medical device or other instrument (for example as described in steps 10 to 13 of Example 1). It will be appreciated that, in some cases, the correct application of the wipe may differ from that described above. For instance, it may not be necessary to wipe from the proximal handle part towards the operative distal part, and in such cases the validation process may determine for example that the wipe has been applied to the whole surface or to a specific area of a medical device.

When a two-part disinfection system is used, such as a chlorine dioxide-based disinfection system described in WO 2005/011756, validation of the steps that ensure correct mixing of the two parts of the disinfection system is useful. However, a single-part disinfecting composition might be appropriate for some applications, and, although not part of the present invention, in these cases validation of other procedural steps, such as the correct selection of products and the correct cleaning of a device, is possible. Single-part disinfecting compositions may include, but are not limited to, hydrogen peroxide, peracetic acids, sodium hypochlorite, peroxy acids, quaternary ammonium compounds, and so on.

The above-described methods and apparatus are not limited to the validation of decontamination processes that use wipes. Substantially any type of product, such as foams, liquids, spray compositions and powders could be used in substantially any combination in a decontamination process and validated using the above-described methods and apparatus. Validation based on the identification of product containers, for example, would still be possible. It would also be possible to train the image analysis module to identify and verify actions such as spraying a medical device with a foam or liquid product or dipping a medical device in a container of liquid.

While the above examples refer to decontamination of a medical device, the validation approach described here can also be applied to decontamination of surfaces or items that cannot readily be placed in the field of view of the camera system. In such cases, validation can for example be performed for the selection of the correct product or sequence of products, and/or the correct mixing of a two-part disinfection system.

Further modifications and variations not explicitly described above may also be contemplated without departing from the scope of the invention as defined in the appended claims.

The invention claimed is:

1. A method, performed by an apparatus including a computer processor, a camera and a memory, for validating a mixing procedure in a process using a two-part disinfectant system, the disinfectant system comprising:

a first part comprising a first reagent in a carrier medium; and a second part which is miscible with the first part and which comprises a second reagent in a carrier medium;

wherein the first reagent and the second reagent will react when mixed to provide a disinfecting composition;

the computer processor being configured to execute a trained neural network that is pre-trained to identify and classify objects and actions associated with the mixing procedure;

the method comprising:

capturing with the camera a video stream of a work area in which the mixing procedure is carried out by a user;

analysing the video stream in real time using the trained neural network executed by the computer processor to identify a sequence of mixing events in the video stream that correspond with the mixing procedure being correctly performed, the sequence of mixing events comprising (i) applying the first part of the disinfectant system to a wipe and, after applying the first part of the disinfectant system to the wipe, (ii) folding or scrunching the wipe to mix the first and second parts together;

determining, using the computer processor, a cumulative time for which folding or scrunching of the wipe has been performed;

comparing, using the computer processor, the cumulative time for which folding or scrunching of the wipe has been performed with a predetermined minimum mixing time retrieved from the memory;

determining, with the computer processor, based on identified sequence of mixing events and the comparison of the cumulative time for which folding or scrunching of the wipe has been performed with the predetermined minimum mixing time, that the mixing procedure has been completed; and upon determining that the mixing procedure has been completed, causing a corresponding indication to be provided to the user.

2. The method according to claim 1, wherein the first part or the second part of the disinfectant system comprises an indicator component that undergoes a colour change upon mixing of the first part and the second part, and wherein identifying the sequence of mixing events comprises identifying the colour change.

3. The method according to claim 1, wherein identifying the sequence of mixing events includes identifying the application of a predetermined quantity of the first part of the disinfectant system to a predetermined quantity of the second part of the disinfectant system.

4. The method according to claim 1, wherein the first part of the disinfectant system is contained in a dispenser whereby it may be dispensed as a fluid, and wherein identifying the sequence of mixing events includes identifying dispensing of the fluid from the dispenser.

5. The method according to claim 1, wherein the second part of the disinfectant system is absorbed or impregnated in the wipe.

6. The method according to claim 1, wherein determining that the mixing procedure has been completed comprises determining, based on the identified sequence of mixing events, that a predetermined quantity of the first part of the disinfectant system has been applied to the wipe.

7. The method according to claim 1, wherein identifying the sequence of mixing events includes identifying the presentation of a container containing the first part or the presentation of a container containing the second part.

8. The method according to claim 1, further comprising:

when analysing the video stream using the trained neural network executed by the computer processor, identifying one or more alert events in the video stream that correspond with potential errors being made during performance of the mixing procedure;

and upon identification of an alert event, causing a corresponding alert to be provided to the user.

9. The method according to claim 8, wherein the alert event comprises shaking a container containing the first part or shaking a container containing the second part.

10. The method according to claim 8, wherein the alert event comprises non-visibility in the work area of an object selected from the group of the user's hands, the first part of the disinfectant system and the second part of the disinfectant system.

11. The method according to claim 8, further comprising electronically logging that an alert event has been identified.

12. The method according to claim 1, comprising electronically logging that the mixing procedure has been completed.

13. The method according to claim 1, comprising electronically logging information concerning the first part of the system and/or the second part of the system, and wherein analysing the video stream comprises identifying, in the video stream, said information concerning the first part of the system and/or the second part of the system.

14. An apparatus for validating a mixing procedure in a process using a two-part disinfectant system, comprising:

a camera system for capturing a video stream of a work area in which the mixing procedure is carried out by a user;

an output device for providing audio, textual or visual indications to the user;

an image analysis module, comprising a neural network-based classifier that is pre-trained to identify and classify objects and actions associated with the mixing procedure, the image analysis module configured to receive the video stream and to identify in real time a sequence of mixing events in the video stream that correspond with the mixing procedure being correctly performed;

the sequence of mixing events comprising (i) applying the first part of the disinfectant system to a wipe and, after applying the first part of the disinfectant system to the wipe, (ii) folding or scrunching the wipe to mix the first and second parts together; and a validator module configured to:

determine, from the sequence of mixing events, a cumulative time for which folding or scrunching of the wipe has been performed;

compare the cumulative time for which folding or scrunching of the wipe has been performed with a predetermined minimum mixing time retrieved from a memory; and determine, based on the identified sequence of mixing events and the comparison of the cumulative time for which folding or scrunching of the wipe has been performed with the predetermined minimum mixing time, that the mixing procedure has been completed, and to cause the output device to provide a corresponding indication to the user upon determining that the mixing procedure has been completed.

15. The apparatus according to claim 14, wherein the image analysis module comprises a neural network-based classifier trained to recognise said one or more mixing events in the video stream.

16. The apparatus according to claim 14, further comprising a logging module configured to electronically log that the mixing procedure has been completed.

17. A decontamination system comprising:

a disinfectant system including:

a first part comprising a first reagent in a carrier medium; and a second part which is miscible with the first part and which comprises a second reagent in a carrier medium;

wherein the first reagent and the second reagent will react when mixed to provide a disinfecting composition;

and an apparatus for validating a mixing procedure in use of the disinfectant system comprising:

a camera system for capturing a video stream of a work area in which the mixing procedure is carried out by a user;

an output device for providing audio, textual and/or visual indications to the user;

an image analysis module, comprising a neural network-based classifier that is pre-trained to identify and classify objects and actions associated with the mixing procedure, the image analysis module configured to receive the video stream and to identify in real time a sequence of mixing events in the video stream that correspond with the mixing procedure being correctly performed;

the sequence of mixing events comprising (i) applying the first part of the disinfectant system to a wipe and, after applying the first part of the disinfectant system to the wipe (ii) folding or scrunching the wipe to mix the first and second parts together; and a validator module configured to:

determine, from the sequence of mixing events, a cumulative time for which folding or scrunching of the wipe has been performed, compare the cumulative time for which folding or scrunching of the wipe has been performed with a predetermined minimum mixing time retrieved from a memory; and determine, based on the identified sequence of mixing events and the comparison of the cumulative time for which folding or scrunching of the wipe has been performed with the predetermined minimum mixing time, that the mixing procedure has been completed, and to cause the output device to provide a corresponding indication to the user upon determining that the mixing procedure has been completed.

* * * * *